(12) United States Patent
Baldock et al.

(10) Patent No.: US 8,650,045 B2
(45) Date of Patent: Feb. 11, 2014

(54) ELECTRONIC HEALTH RECORD SHARING USING HYBRID ARCHITECTURE

(75) Inventors: Daniel James Baldock, Portland, OR (US); Vadim Georgiovich Svinenko, Vancouver, WA (US); Kerri E. Marshall, Portland, OR (US); Karen Calhoun, Portland, OR (US)

(73) Assignee: Medical Management International, Inc., Portland, OR (US)

( * ) Notice: Subject to any disclaimer, the term of this patent is extended or adjusted under 35 U.S.C. 154(b) by 187 days.

(21) Appl. No.: 12/874,896

(22) Filed: Sep. 2, 2010

(65) Prior Publication Data

US 2012/0059668 A1    Mar. 8, 2012

(51) Int. Cl.
*A61B 5/00* (2006.01)

(52) U.S. Cl.
USPC ......... 705/3; 705/2; 705/51; 380/28; 713/193

(58) Field of Classification Search
USPC ....... 705/2, 3, 51; 707/103; 380/28; 704/270; 713/193
See application file for complete search history.

(56) References Cited

U.S. PATENT DOCUMENTS

| | | | | |
|---|---|---|---|---|
| 6,047,257 | A * | 4/2000 | Dewaele | 704/270 |
| 7,328,222 | B2 * | 2/2008 | Keith et al. | 1/1 |
| 7,613,620 | B2 * | 11/2009 | Salwan | 705/2 |
| 7,869,591 | B1 * | 1/2011 | Nagel et al. | 380/28 |
| 7,953,614 | B1 * | 5/2011 | Reicher et al. | 705/3 |
| 8,102,254 | B2 * | 1/2012 | Becker et al. | 340/539.12 |
| 8,457,990 | B1 * | 6/2013 | Reicher et al. | 705/3 |
| 2001/0049610 | A1 * | 12/2001 | Hazumi | 705/3 |
| 2002/0103811 | A1 | 8/2002 | Fankhauser et al. | |
| 2005/0071194 | A1 | 3/2005 | Bormann et al. | |
| 2005/0246205 | A1 | 11/2005 | Wang et al. | |
| 2006/0174335 | A1 | 8/2006 | Jorgenson | |
| 2007/0214016 | A1 | 9/2007 | Bennett et al. | |
| 2008/0046292 | A1 | 2/2008 | Myers et al. | |
| 2008/0052113 | A1 | 2/2008 | Cauley et al. | |
| 2008/0052115 | A1 | 2/2008 | Spradley et al. | |
| 2008/0133273 | A1 | 6/2008 | Marshall | |
| 2008/0177576 | A1 | 7/2008 | Jennings et al. | |
| 2008/0183495 | A1 | 7/2008 | Butterfield et al. | |
| 2008/0208625 | A1 | 8/2008 | Joseph | |
| 2008/0243539 | A1 | 10/2008 | Barish et al. | |
| 2009/0012817 | A1 | 1/2009 | Squires et al. | |
| 2009/0037334 | A1 * | 2/2009 | Hsu et al. | 705/51 |
| 2009/0076852 | A1 | 3/2009 | Pierson et al. | |
| 2009/0080408 | A1 | 3/2009 | Natoli et al. | |
| 2009/0193267 | A1 * | 7/2009 | Chung | 713/193 |
| 2009/0216562 | A1 | 8/2009 | Faulkner et al. | |

OTHER PUBLICATIONS

Google patents search, Sep. 20, 2013.*

(Continued)

*Primary Examiner* — Dilek B Cobanoglu
(74) *Attorney, Agent, or Firm* — Klarquist Sparkman, LLP

(57) ABSTRACT

Electronic health record sharing is provided using a hybrid architecture. A centralized architecture provides centralized service including a search service and a token ownership service. A decentralized architecture comprises electronic health record locations. Electronic health records are created at locations and patient identifying information is stored at the centralized architecture. The centralized service manages ownership of electronic health records using ownership tokens comprising unique electronic health record identifiers and unique location identifiers. A current electronic health record owner location is authorized to view and/or edit the electronic health record. Ownership is transferred via the sending location, receiving location, and centralized service.

12 Claims, 9 Drawing Sheets

(56) References Cited

OTHER PUBLICATIONS

Google prior art search, Oct. 2, 2013.*

Credential based hybrid access control methodology for shared Electronic Health Records, 2009 International Conference on Information Management and Engineering, Nirmal Dagdee, Ruchi VIjaywargiya, SD Bansal College of Technology.*

Wikipedia, "Concurrency control," <http://en.wikipedia.org/wiki/Concurrency_control>, 4 pages (accessed Sep. 1, 2010).

Wikipedia, "Globally unique identifier," <http://en.wikipedia.org/wiki/Guid>, 6 pages (accessed Sep. 1, 2010).

Wikipedia, "Hospital information system," <http://en.wikipedia.org/wiki/Hospital_information_system>, 2 pages. (accessed Sep. 1, 2010).

Wikipedia, "Electronic medical record," <http://en.wikipedia.org/wiki/Electronic_medical_record>, 5 pages (accessed Sep. 1, 2010).

Wikipedia, "Health information exchange," <http://en.wikipedia.org/wiki/Health_information_exchange>, 5 pages (accessed Sep. 1, 2010).

Wikipedia, "Health informatics," <http://en.wikipedia.org/wiki/Health_informatics>, 9 pages (accessed Sep. 1, 2010).

Wikipedia, "Continuity of Care Record," <http://en.wikipedia.org/wiki/Continuity_of_care_record>, 2 pages (accessed Sep. 1, 2010).

Neil Versel, "Health Information Exchange: Patient Data on the Move," CMIO, pp. 4-7 (Sep. 23, 2009).

* cited by examiner

ELECTRONIC HEALTH RECORD SHARING USING HYBRID ARCHITECTURE

BACKGROUND

Global computerization and technological advancements in medicine and integration with medical equipment have enabled the healthcare industry to manage patient records in a more productive and organized way, principally by utilizing any one of a number of electronic health record (EHR) systems that are commercially available. Many EHR systems provide specialized workflows and enhanced functionality for healthcare professionals but often these systems are stand-alone and cannot exchange information across multiple locations or multiple systems. Patients visiting multiple medical facilities cannot fully benefit because these EHR systems do not have any way to locate or exchange medical data between systems or between two instances of the same system.

This fragmented nature of medical records can make it difficult for patients and healthcare professionals to obtain a full, consistent, and complete medical history (i.e. a longitudinal medical record) in order to provide the best care. Without the ability to share records, healthcare costs increase when diagnostic and laboratory tests are duplicated at another facility because they do not have access to results from the previous institution. A nationwide health information exchange with secure and quick sharing of data between stakeholders and systems, and between platforms, is needed in order to have an effective public health system. A complete longitudinal health record for all patients can be achieved with a functional nationwide health information exchange.

Health information exchange (HIE) platforms are being developed using existing methods of data interchange and standardized formats like those developed by HL7 (Health Level Seven International) and DICOM (Digital Imaging and Communications in Medicine). These existing platforms require centralized or common data storage (e.g. Microsoft® HealthVault™), or agreements that allow provider organizations to mutually sign-on to each other's systems. Standards harmonization must occur between each stakeholder and the nationwide health information network (NHIN) in order to create a nationwide health information exchange. The persistent issue in these approaches is the uncertainty that the record set to be accessed with some type of operation (e.g., create, read, update, or delete operation (CRUD)) is actually the most current and complete record set. Given that the data is "live" in multiple systems and concurrent operation actions are likely, the healthcare provider may not be working with the most up to date data. With current approaches to data interchange, healthcare providers can't be sure. Clearly, there is a need to reliably locate and easily, but securely, share electronic health records across multiple medical facilities with assurance the record set retrieved is the last updated and most comprehensive.

Therefore, there exists ample opportunity for improvement in technologies related to sharing electronic health records.

SUMMARY

A variety of technologies related to sharing electronic health records are applied.

For example, a method is provided for controlling access to electronic health records using a hybrid architecture by obtaining, by a first location from a centralized service, a unique health record (EHR) identifier identifying an EHR of a patient and an associated unique location identifier identifying a second location, copying the EHR from the second location directly to the first location, and transferring ownership of the EHR, via the centralized service, from the second location to the first location. The transfer of ownership is required before the first location is authorized to make changes to the EHR (e.g., the EHR is locked, such as with a pessimistic lock, before the location obtaining the lock can update the EHR). The centralized service is part of a centralized architecture, and the first location and the second location are part of a distributed architecture separate from the centralized architecture. The hybrid architecture comprises the centralized architecture and the distributed architecture.

As another example, a method is provided for controlling access to electronic health records using a hybrid architecture by obtaining, by a first location from a token ownership service of a centralized service, an ownership token comprising a unique electronic health record (EHR) identifier identifying EHR of a patient and a unique location identifier identifying a second location, where the second location currently owns the EHR, and where the second location currently stores the EHR. The method further comprises sending, from the first location directly to the second location, a request to transfer the EHR stored at the second location, receiving, at the first location directly from the second location, the EHR, and obtaining, by the first location from the token ownership service and from the second location, ownership of the EHR, where the ownership is obtained, at least in part, using a pessimistic lock, and where obtaining ownership is required before the first location is authorized to make changes to the EHR. The centralized service is part of a centralized architecture, and the first location and the second location are part of a distributed architecture separate from the centralized architecture.

As another example, a system is provided for controlling access to electronic health records using a hybrid architecture, comprising a token ownership service as part of a centralized service of a centralized architecture and a search service as part of the centralized service of the centralized architecture. The token ownership service is configured for storing an ownership token, where the ownership token comprises a unique electronic health record (EHR) identifier identifying an EHR of a patient and a unique location identifier, associated with the unique EHR identifier, identifying a first location, where the first location currently owns the EHR of the patient. The search service is configured for storing patient identifying information of the patient, where the patient identifying information is associated with the unique EHR identifier of the patient, and where the patient identifying information is a subset of patient information stored in the EHR, and for responding to a search request by looking up the ownership token based on at least some of the patient identifying information. The centralized architecture provides the centralized service to a plurality of locations, where the plurality of locations are part of a distributed architecture, where the distributed architecture is separate from the centralized architecture, where the EHR is stored at a first location of the plurality of locations, and where the EHR is not stored at the centralized architecture.

In a specific implementation, an approved provider or facility (e.g., a specific EHR location) may simply view a patient's medical history without taking token ownership, but must take token ownership in order to update client information and add medical information to the patient's medical records. The process allows a provider to build on the patient's medical record by adding new medical information, thus creating a longitudinal medical record for each patient, while enforcing integrity of medical history for that patient by prohibiting editing of historical information.

The foregoing and other features and advantages of the invention will become more apparent from the following detailed description, which proceeds with reference to the accompanying figures.

DETAILED DESCRIPTION OF EXEMPLARY EMBODIMENTS

Figure 1:
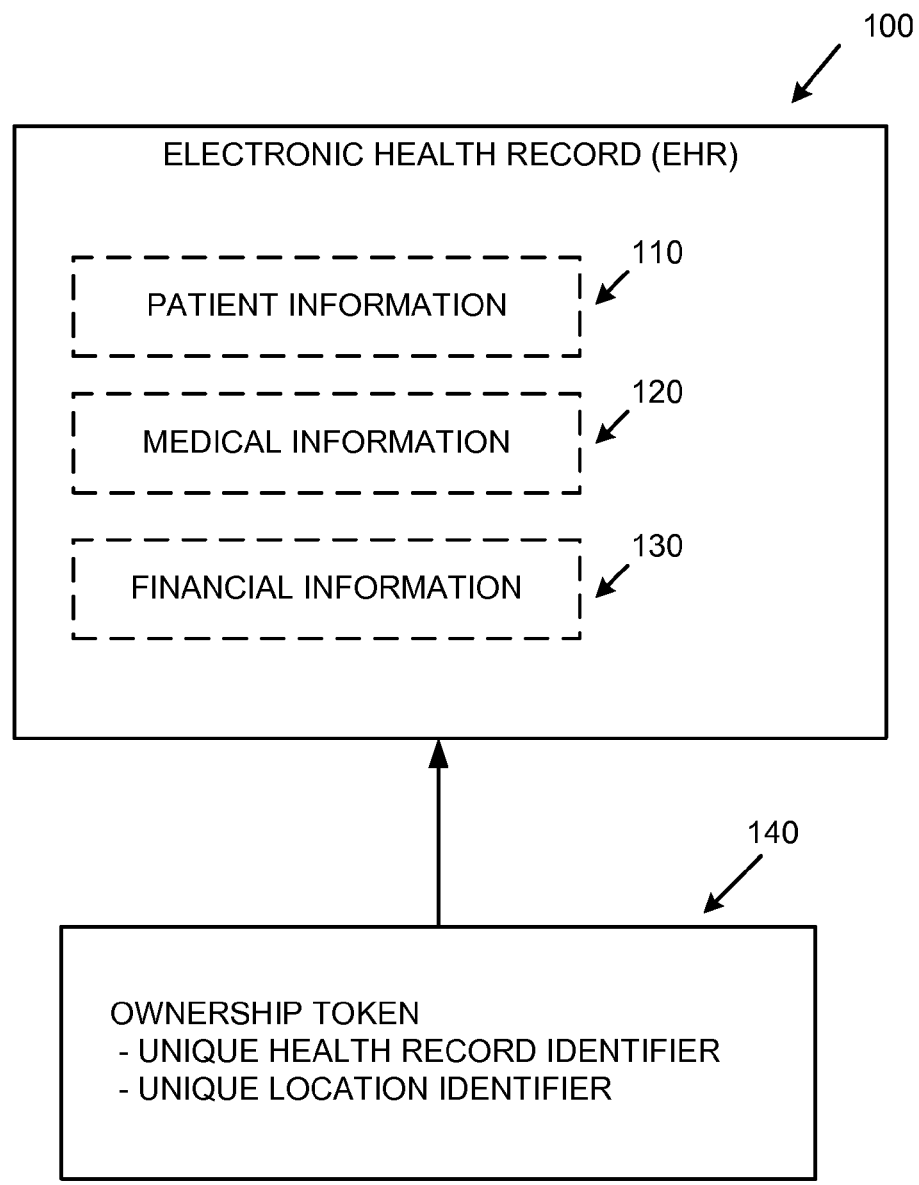
FIG. 1 is a diagram showing an example electronic health record and associated ownership token.

The following description is directed to techniques and solutions for electronic health record sharing. The various techniques and solutions can be used in combination or independently. Different embodiments can implement one or more of the described techniques and solutions.

I. Example Electronic Health Record

An electronic health record (EHR) (also called an electronic medical record (EMR)) is a collection of electronic information or data related to the health of a patient. An electronic health record refers to an electronic representation of the patient's health information. For example, an electronic health record can refer to structured or unstructured data (e.g., patient information, medical information, financial information, and/or client information) stored in a database (e.g., stored in one or more database records of a relational database).

A patient can be a human patient or an animal patient (e.g., a pet, such as a cat or a dog). Some examples of electronic health record information are: patient information (e.g., name, address, phone number, date of birth, social security number, etc.), medical information (e.g., medical facility information, notes—such as those entered by a doctor, test results, x-rays, prescribed medications, professional services provided, etc.), financial information (e.g., billing information, insurance information, payment information, transaction history, etc.), and client information (note that in a veterinary setting, the patient is the pet and the pet owner is called the client). Electronic health record information can also include information maintained by the patient (e.g., information from a personal health record (PHR) or electronic personal health record (ePHR)). The type of information included in an electronic health record depends on the health system, and may include some or all (or none) of the example information listed above in addition to other healthcare related information.

Electronic health records can be identified by various information included in the electronic health record (e.g., name, social security number, phone number, etc.), by various types of unique identifiers, or by other means. In a specific implementation, electronic health records are identified by unique patient identifiers. In a specific implementation, a unique patient identifier is a globally unique identifier (GUID).

Electronic health records can be associated with a location (e.g., a medical facility, hospital, clinic, department, etc.) that has current ownership over the electronic health record. In a specific implementation, the location is identified by a unique location identifier. In a specific implementation, a unique location identifier is a globally unique identifier (GUID).

In a specific implementation, ownership of an electronic health record refers to the exclusive right to modify (e.g., add, edit, and/or delete) information in the electronic health record.

In a specific implementation, electronic health records are uniquely identified via globally unique identifiers (GUIDs) to eliminate any data collisions. Because GUIDs are guaranteed to be unique, in the event of physical record transfer, unique primary key database constraints will not be violated and complex merge logic and key re-assignment can be all avoided.

FIG. 1 shows an example electronic health record and associated ownership token. The electronic health record 100 includes patient information 110, medical information 120, and financial information 130. As discussed above, the EHR 100 can include other types of health-related information in addition to, or instead of, the listed information (110, 120, and 130).

The EHR 100 is associated with an ownership token 140. The ownership token 140 includes a unique health record identifier (e.g., a GUID) that uniquely identifies the EHR 100. The ownership token 140 also includes a unique location identifier (e.g., a GUID) that uniquely identifies the location that currently owns (e.g., has obtained a pessimistic lock for) the EHR 100. The EHR 100 may also include a copy of the unique health record identifier and/or the unique location identifier (e.g., to aid in identifying the EHR 100).

In a specific implementation, the electronic health records (e.g., EHR 100) are stored at individual locations of a distributed architecture, and the ownership tokens (e.g., ownership token 140) are stored at a centralized service of a centralized architecture.

II. Example Hybrid Architecture for Controlling Access to Electronic Health Records The electronic health record sharing solutions described herein are based on a hybrid approach where functionality is split between a centralized architecture and a distributed architecture. The distributed architecture provides durability, availability, security, and performance regardless of the quality of the external network connections, and the centralized architecture provides centralized services comprising a search service and a token ownership service. This combination of centralized and distributed architectures allows for electronic health record (EHR) systems independence while providing unified health record search, transfer, and ownership management.

Figure 2:
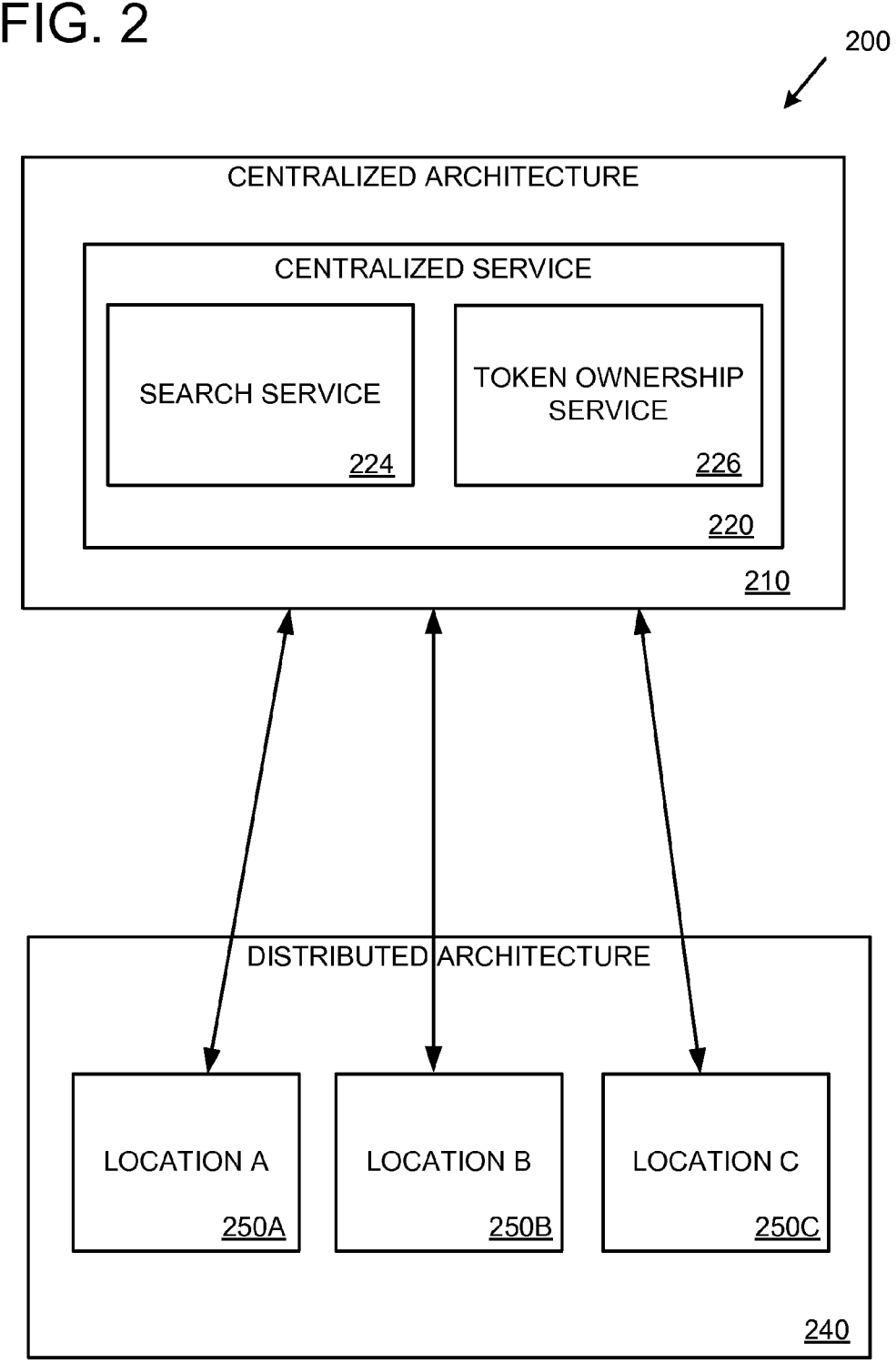
FIG. 2 is a diagram showing an example hybrid architecture for electronic health record sharing.

FIG. 2 shows an example hybrid architecture 200 for electronic health record sharing. The hybrid architecture 200 supports electronic health record sharing by controlling access to electronic health records. The hybrid architecture 200 depicts architecture detail for a specific implementation that supports EHR sharing. In different implementations, components depicted in the hybrid architecture can be rearranged, modified, and/or deleted.

The example hybrid architecture 200 includes a centralized architecture 210. The centralized architecture 210 provides centralized services 220 supporting electronic health record sharing. In the example hybrid architecture 200, the centralized architecture 220 provides two services, a search service 224 and a token ownership service 226. In other implementations, other services can be provided by the centralized service 220 (e.g., a router service and/or an enterprise messaging service).

Figure 6:
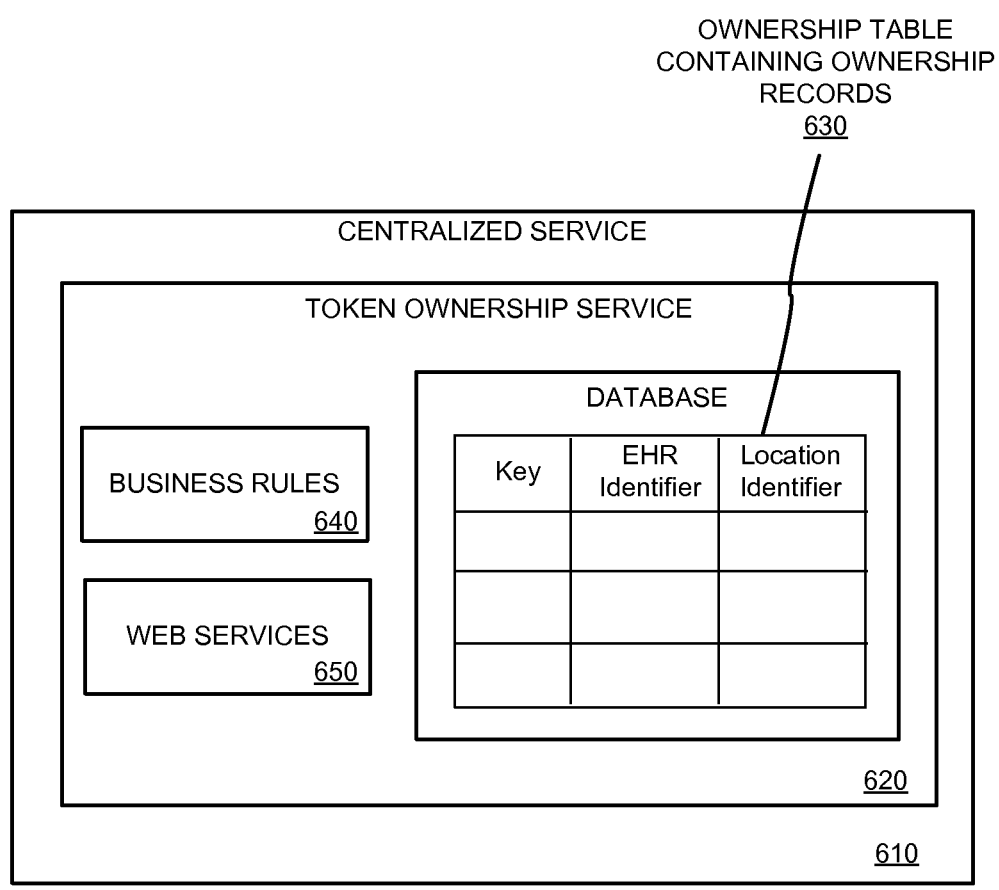
FIG. 6 is a diagram showing an example token ownership service.

The token ownership service 226 controls ownership of electronic health records using ownership tokens. In a specific implementation, ownership tokens are stored by the token ownership service 226 in ownership records in a database (e.g., as depicted in FIG. 6). An ownership token comprises a unique electronic health record (EHR) identifier identifying an EHR of a patient, and a unique location identifier identifying a location that currently owns the EHR of the patient.

The search service 224 stores patient identifying information associated with electronic health records. For example, the patient identifying information can include name, address, phone number, social security number, or other identifying information. The patient identifying information is associated with an electronic health record for that patient (e.g., the patient identifying information for a specific patient can include an electronic health record GUID for the EHR of the patient). In a specific implementation, patient identifying information for each patient in the search service 224 is associated with its respective electronic health record via a unique electronic health record identifier stored in an ownership token by the token ownership service 226.

The search service 224 responds to search requests for electronic health records by looking up electronic health records (e.g., EHR GUIDs) based on patient identifying information. For example, a EHR location trying to locate the EHR for the patient named "John Doe" could send the patient identifying information (the name "John Doe") to the search service 224. The search service 224 could look up the name "John Doe" in its database and locate a record associating patient "John Doe" with the patient's specific electronic health record (e.g., a specific electronic health record with a unique identifier of 1234-abcd-5678-defg).

The distributed architecture 240 comprises any number of locations, such as locations A, B, and C (250A, 250B, and 250C). The different locations (e.g., 250A, 250B, and 250C) are locations at which electronic health records are owned, stored, and used. For example, the locations (e.g., 250A, 250B, and 250C) can be individual hospitals, departments, clinics, or other health provider related locations. A location such as a hospital can represent a single location, or it can be divided into multiple locations (e.g., into multiple department locations of the hospital). A location (e.g., 250A, 250B, or 250C) can obtain ownership of an electronic health record by sending a request to the search service 224 to look up the electronic health record and sending a request to the token ownership service 226 to transfer ownership to that location.

In a specific implementation, each EHR location (e.g., 250A, 250B, and 250C) participating in the electronic record sharing hybrid architecture 200 comprises its own database with a full set of the electronic health records currently owned by that location. For example, if location A (250A) currently owns ten electronic health records (as managed by the token ownership service 226) then those ten electronic health records (e.g., comprising client information, medical information, and/or financial information) would be stored by location A (250A).

In a specific implementation, the electronic health records are not stored by the centralized architecture 210. Instead, only a small subset of the patient identifying information (e.g., name, address, phone number) along with the unique electronic health record identifier and the unique location identifier are stored by the centralized service 220.

The hybrid architecture 200 uses pessimistic locking to ensure that any given electronic health record is owned by no more than one location at any given time. Any given electronic health record can be viewed by any number of locations, however it can only be owned by a single location at any given time. This pessimistic locking for electronic health record ownership guarantees data consistency across the entire architecture 200 and is managed by the centralized architecture 210 (mainly by the token ownership service 226).

The ownership token service 226 is a single authority of electronic health record ownership and points to the specific location of the owner (if any) at any given time. Token ownership service 226 is durable and reliable, and can be implemented via ACID (atomic, consistent, isolated, durable) enterprise databases and exposed as a web service.

The centralized architecture 210 and distributed architecture 240 are connected via a connecting network. The connecting network can be a local area network, a wide area network (e.g., a private enterprise WAN), a public network (e.g., the Internet), a private network, or another type of connecting network. For example, the connecting network can be a distributed private network of a single health care organization (e.g., a national hospital system comprising many separate locations). In a specific implementation, the connecting network comprises an enterprise messaging bus and an enterprise messaging server.

In a specific implementation, new electronic health records (e.g., for new patients) are created at locations (e.g., 250A, 250B, and 250C) within the distributed architecture 240. The locations (e.g., 250A, 250B, and 250C) notify (e.g., send or broadcast) information related to the newly created electronic health records to the centralized service 220 so the search service 224 can be updated and new ownership tokens can be created by the token ownership service 226. After creation, the ownership token for the electronic health record will be retained within the token ownership service 226 until another location makes a request for transfer of ownership. If the record is available for transfer (ownership is not currently locked at another location), the electronic health record will be transferred from the current owner location to the requesting location followed by a 3-way transaction (between the current location, the requesting location, and the token ownership service) to commit the ownership change. Using an atomic 3-way transaction provides data consistency within the entire health record sharing system.

For example, a patient (who does not already have an electronic health record in the system 200) visiting location A (250A) will have a new EHR created by location A (250A). Location A (250A) will then send patient identifying information (e.g., patient name and address) to the centralized service 220 along with the unique EHR identifier and the unique location identifier for location A (250A). The centralized service 220 will use the received information to update the search service 224 and create the ownership token for the new EHR via the token ownership service 226.

In a specific implementation, the search service 224 provides a fast and unified way of locating patient electronic health records and assists in determining the exact ownership location. Every time a new electronic patient record is created in any EHR location participating within the record sharing architecture 200, a new message is generated and sent to the search service 224 and token ownership service 226 in near real time, so the services are updated and stay current. Similarly, any relevant updates to the patient identifying information at any location are also sent to the search service 224. All EHR locations can utilize search service 224 to locate patient electronic health records and, using the token ownership service 226, can transfer ownership.

In a specific implementation, each EHR location (e.g., 250A, 250B, and 250C) utilizes an enterprise class messaging bus to communicate events such as the creation and modification of the electronic health records to the centralized service 220. The enterprise communications can be optionally encrypted to provide additional security and privacy of the electronic health record. The enterprise messaging bus is highly available, durable, and secure and guarantees delivery of all messages in transactional fashion. The enterprise message bus also provides a security audit record for all transactions that take place within the health record sharing enterprise (e.g., extensive transaction and event logging).

In a specific implementation, electronic health records are sent and received directly using peer-to-peer connections between the locations (e.g., 250A, 250B, and 250C). While the transfer of ownership (involving the ownership tokens stored by the token ownership service 226) utilizes the centralized architecture 210, the sending and receiving of the actual electronic health records (e.g., compressed electronic health records packets comprising patient information, medical information and/or financial information) are communicated directly between the locations, without communicating them to the centralized architecture 210.

While the centralized architecture 210 and distributed architecture 240 are separate architectures, they are not necessarily located at different physical locations. In some implementations, the centralized architecture 210 is located at a separate physical location from the EHR locations (e.g., 250A, 250B, and 250C). For example, the centralized architecture 210 can be located at a data center or central office of an organization. In other implementations, the centralized architecture 210 is located at the same physical location as one or more of the EHR locations (e.g., 250A, 250B, or 250C). For example, the centralized architecture 210 could be operated by computer servers located at a centralized hospital, and the centralized hospital could also be one of the locations (e.g., location 250A). In addition, the centralized architecture 210 can support other EHR locations at different physical locations (e.g., locations 250B and 250C).

III. Example Methods for Controlling Access to Electronic Health Records

Controlling access to electronic health records using a hybrid architecture involves a number of related operations, which can include: creating electronic health records, sending identifying information to a centralized search service, creating centralized search and token ownership service information for newly created electronic health records, searching for electronic health records, sending/receiving electronic health records between locations, editing and modifying information stored in electronic health records, view-only capabilities, and transferring ownership of electronic health records.

In a specific implementation, the following represents an example workflow for locating and taking ownership of an electronic health record. First, a search is performed with specific search criteria (e.g., patient identifying information) to obtain a list of matches from the search service via a synchronous web services call. The result of the search contains various data elements to uniquely identify the patient (e.g., name, address, phone number) as well as a unique electronic health record identifier and the current owner location unique identifier. After the specific record is selected from the list, the requesting location sends a record transfer request directly (via a peer-to-peer connection) to the owner location without any need for centralized service intervention. The current owner location processes the request and evaluates possibility of transfer based on the current electronic health record use. If the record is currently in use (e.g., the record is locked for editing, such as when the patient is currently checked-in to the location), the transfer is denied. However, if the record is not currently in use, an electronic health record package is created (e.g., a compressed data package comprising the electronic health record information, such as patient information, medical information, and/or financial information) and transfer is allowed. When the current owner delivers the record sharing package directly to the requesting location (peer-to-peer) and as soon as data transfer is successfully completed, a 3-way transaction is executed between the requesting location, the current owner location, and the central token ownership service to change ownership to the requesting location. Any subsequent searches for the newly transferred electronic health record will point to the new owner location. The electronic health record can be transferred any number of times and as frequently as necessary (so long as it is not currently locked).

In many cases an electronic health record just needs to be viewed (read) instead of modified or added to. In case of a view (or read) request, actual ownership of the electronic health record does not need to change. In a specific implementation, the following is an example workflow for locating and viewing an electronic health record. First, a search is performed with the specific search criteria (e.g., patient identifying information) to obtain a list of matches from the search service via a synchronous web services call. The result of the search contains various data elements to uniquely identify the patient (i.e. name, address, phone number) as well as a unique electronic health record identifier and the current owner location unique identifier. After a specific record is selected from the list, the requesting location sends a record view request directly (via a peer-to-peer connection) to the owner location without any need for involvement by the centralized service. The current owner processes the request and an electronic health record package is created (e.g., a compressed data package comprising the electronic health record information, such as patient information, medical information, and/or financial information). The current owner delivers the electronic health record package directly to the requesting location (via the peer-to-peer connection). Ownership of the electronic health record is retained with the current owner (it does not transfer to the location receiving the read-only copy of the record) and no further action is required.

Figure 3:
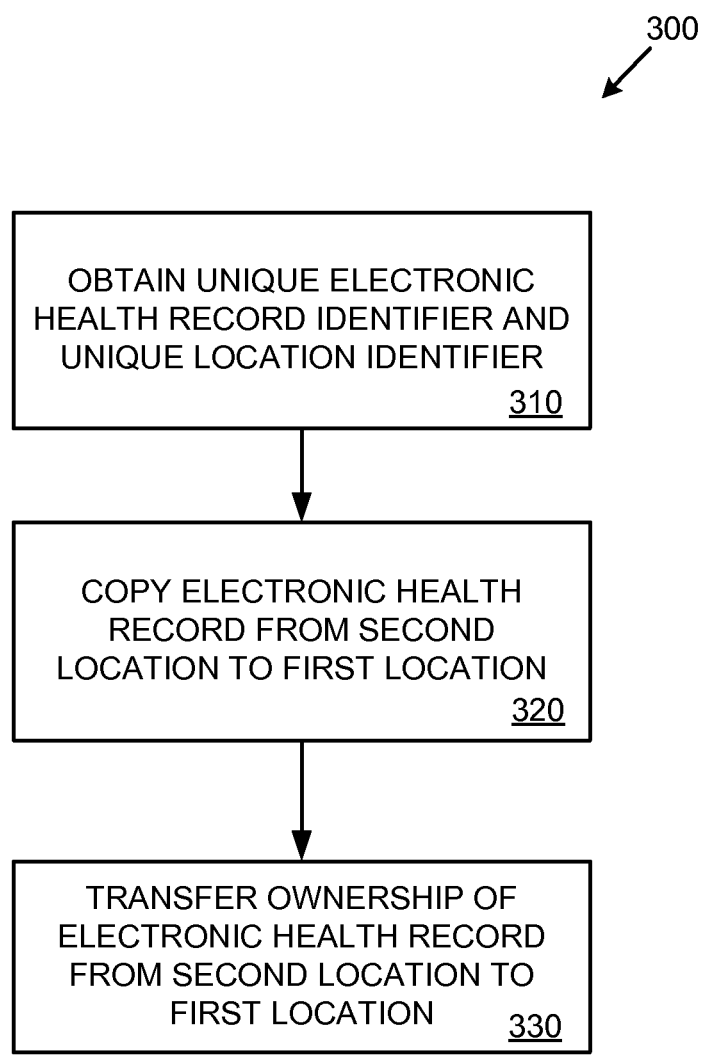
FIG. 3 is a flowchart showing an example method for controlling access to electronic health records using a hybrid architecture.

FIG. 3 shows an example method 300 for controlling access to electronic health records using a hybrid architecture. At 310, a unique electronic health record identifier (e.g., an EHR GUID) and a unique location identifier (identifying a second location that currently owns the EHR) are obtained by a first location from a centralized service (e.g., comprising a search service and a token ownership service). For example, the first location can send a search request (e.g., comprising patient identifying information) to a centralized service and receive the unique electronic health record identifier and the unique location identifier from the centralized service.

At 320, the electronic health record is copied from the second location to the first location. For example, the electronic health record can be copied directly (e.g., via a peer to peer network connection) without involvement by the centralized service.

At 330, ownership of the electronic health record is transferred from the second location to the first location. The transfer is performed, at least in part, using the centralized service. In a specific implementation, the transfer involves a three-way transaction between the first location, second location, and a token ownership service of the centralized service. In addition, the transfer can involve obtaining a pessimistic lock on the electronic health record (e.g., as part of the three-way transaction).

Figure 4:
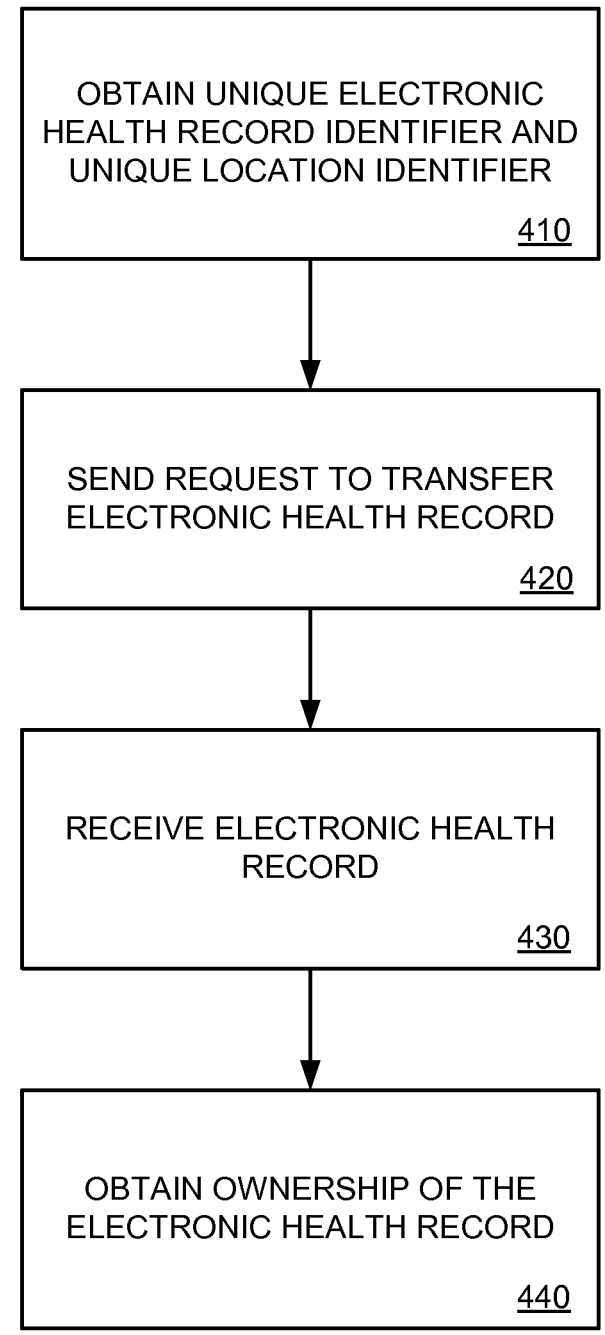
FIG. 4 is a flowchart showing an example method for controlling access to electronic health records using a hybrid architecture comprising a centralized architecture and a distributed architecture.

FIG. 4 shows an example method 400 for controlling access to electronic health records using a hybrid architecture comprising a centralized architecture and a distributed architecture. At 410, a unique electronic health record identifier (e.g., an EHR GUID) identifying an electronic health record of a patient, and a unique location identifier (identifying a second location that currently owns the EHR) are obtained by a first location from a centralized service (e.g., comprising a search service and a token ownership service). For example, the first location can send a search request (e.g., comprising patient identifying information) to a centralized service and receive the unique electronic health record identifier and the unique location identifier from the centralized service.

At 420, the first location sends a request directly to the second location to transfer the electronic health record. In a specific implementation, the request is sent via a peer-to-peer connection between the first and second locations, without involvement by the centralized service.

At 430, the first location receives the electronic health record (e.g., an electronic health record package comprising patient information, medical information, and financial information for the patient) from the second location. In a specific implementation, the electronic health record is received via a peer-to-peer connection between the first and second locations, without involvement by the centralized service.

At 440, the first location obtains ownership of the electronic health record from the centralized service. In a specific implementation, the transfer of ownership of the electronic health record from the second location to the first location involves a three-way transaction between the first location, second location, and a token ownership service of the centralized service. In addition, the transfer can involve obtaining a pessimistic lock on the electronic health record (e.g., as part of the three-way transaction).

IV. Example Hybrid Architecture Details

Figure 5:
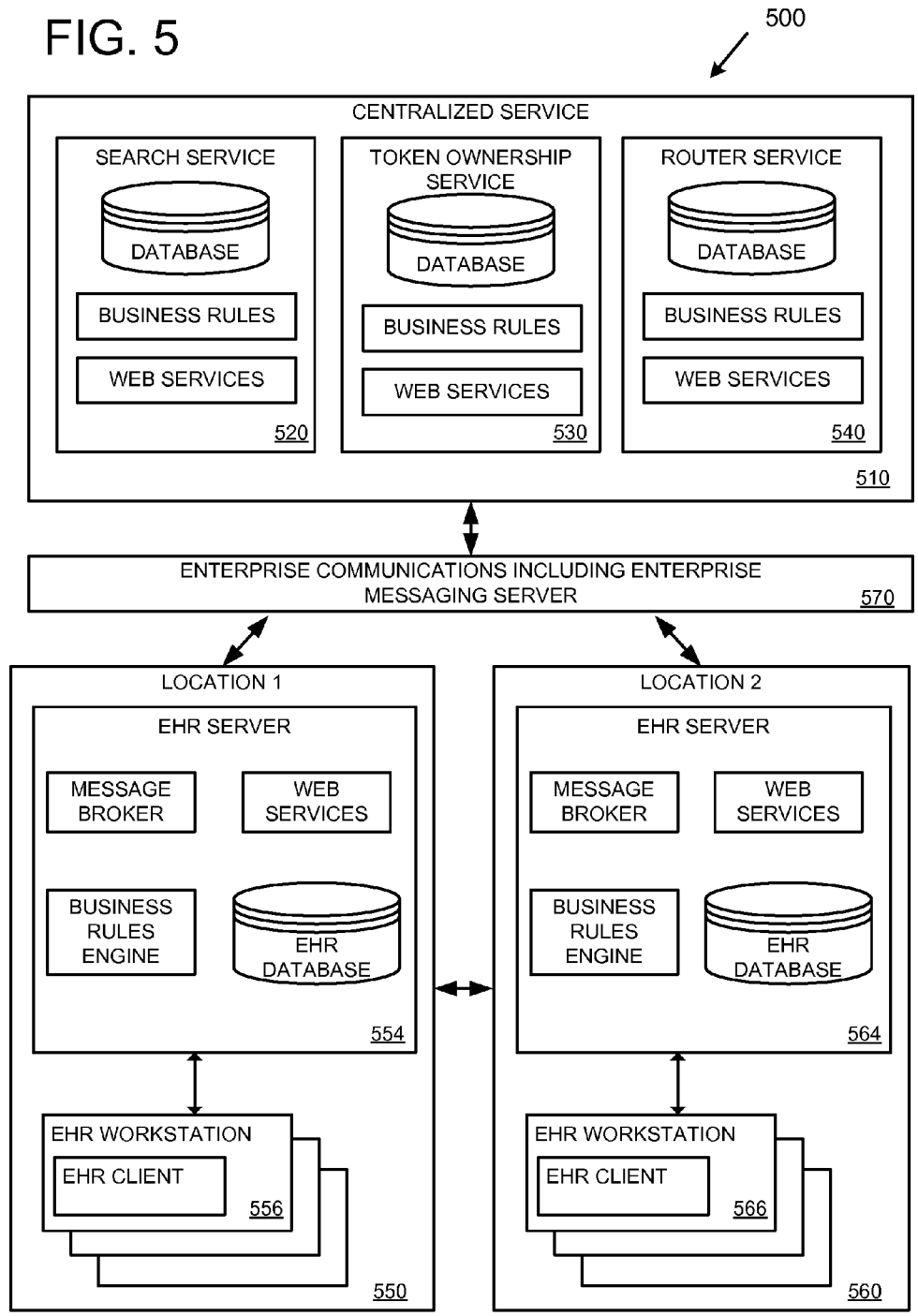
FIG. 5 is a diagram showing an example of a detailed architecture for supporting electronic health record sharing.

FIG. 5 shows an example of a detailed hybrid architecture 500 supporting electronic health record (EHR) sharing. The hybrid architecture 500 supports electronic health record sharing by controlling access to electronic health records. The hybrid architecture 500 depicts architecture detail for a specific implementation that supports EHR sharing. In different implementations, components depicted in the hybrid architecture can be rearranged, modified, and/or deleted.

FIG. 5 is an example hybrid architecture diagram showing elements of an enterprise architecture used to create a durable, secure and high performance health record sharing solution. As shown in the diagram 500, the architecture consists of three main components: distributed EHR solutions 550 and 560, enterprise communications and enterprise messaging server 570, and centralized services 510 (including a search service 520, token ownership service 530 and router service 540).

Distributed EHR solutions 550 and 560 are fully functional stand-alone systems, available regardless of the quality of the external network connection. This availability and durability is achieved by having a local database associated with the EHR server system (554 and 564) with the full set of data necessary for EHR workflows. The example hybrid architecture 500 can contain any number of participating EHR locations, such as EHR location 1 (550) and EHR location 2 (560). Each EHR location can contain any number of EHR workstations (e.g., 556 and 566), which access EHR data stored in the EHR database on respective EHR server systems (554 or 564). The EHR database can be ACID (Atomicity, Consistency, Isolation, and Durability are properties of a DBMS—Data Base Management System) compliant, enterprise class database, secure, reliable and durable to ensure integrity, durability and availability of the electronic medical record.

The EHR server systems (554 and 564) also contain business rules engines to provide a consistent way to access and manipulate EHR data regardless of what service or EHR client is accessing it. The EHR workstations access their respective EHR server system (554 or 564) via a local area network (LAN) and use the EHR database as a source of EHR data.

The EHR server systems (554 and 564) also contain message brokers and a set of web services for external communications. The message broker is used for asynchronous messages arriving to the distributed EHR locations (550 and 560) or going out to the central services 510. The web services are used for synchronous messages coming from and to the EHR server systems (554 and 564). The combination of message broker and web services provides a durable, highly reliable and secure communication channel to the enterprise communications/enterprise messaging server 570 (e.g., comprising a message store database). The message broker is durable and consists of persistent data store for all inbound and outbound messages. Having a persistent data store allows for transactional message processing and guarantees no data loss while messages are in transit. The web services can be encrypted to secure communication channels and protect privacy of the medical information. The web services and message queues adhere to well defined contracts published by the enterprise messaging server 570 to ensure consistency and compatibility of data exchange within the entire record sharing architecture 500.

The enterprise messaging server 570 (which could be, for example, Microsoft® BizTalk® or IBM® WebSphere®) is highly reliable and durable. This enterprise messaging server 570 is in the role of the information broker; data exchange (except peer-to-peer communications between locations) is durable, reliable, secure, tracked, logged and routed. Enterprise messages, inbound and outbound, adhere to the well formatted contracts (interfaces) and are routed according to the business rules of the enterprise messaging server 570. The enterprise messaging server 570 encapsulates enterprise the messaging environment and segregates individual EHR locations from external vendors and services. In some cases EHR systems (e.g., centralized service 510 and/or locations 550 and 560) need to either use services of an external vendor or exchange information with external systems. For external communications, the enterprise messaging server 570 is responsible for routing messages and web service calls to the appropriate owner (e.g., of an external electronic health record system). This way, external systems are not aware of the physical location of the information and do not need to implement location services or deal with timing issues or conflict resolution. Effectively, the enterprise messaging server 570 hides complexities of record sharing and makes communication simpler and more reliable.

Centralized services 510 include three services: a search service 520, a token ownership service 530 and a router service 540. The search service 520 is a catalog of searchable patient information, aggregated from participating EHR locations (such as 550 and 560) and is designed to provide a quick and efficient way to find patient electronic health record within the entire health information exchange. The search service 520 can provide electronic health record information for a business or organization (e.g., within a single health care company, which can have one or more locations) or for a group of related or affiliated businesses or organizations (e.g., a regional, national, or global network of affiliated health care providers or organizations). The search service 520 is updated (e.g., in near real time or at some consistent interval) to ensure accuracy and consistency of the catalog.

The token ownership service 530 contains ownership information for electronic health records available within the record sharing system. An electronic health record can only be owned (for modification, such as editing or updating) by one location at any given time. The ownership token is a unique electronic health record identifier paired with a unique EHR location identifier (e.g., see FIG. 6). The ownership token service 530 is a durable, highly available, and reliable service, and is important for communications as the current owner of the electronic health record needs to be identified, and ownership transferred to a new owner, before any transaction to update the electronic health record takes place. Other business rules may be added to govern the transfer of the ownership token within the health information exchange (HIE), but an important concept is that only the current owner of an electronic health record can edit the record.

The router service 540 is responsible for routing messages to the correct electronic health record system based on the token ownership service 530. The ownership of the record is dynamic and can change at any time and as many times as necessary, so centralized services 510 are updated via enterprise communications 570 and web services (e.g., in near real time) to provide accurate, consistent, and reliable electronic health record location information to the entire record sharing enterprise.

V. Example Token Ownership Service

FIG. 6 shows an example token ownership service 620. For example, the token ownership service 620 can be the token ownership service depicted at 530 in FIG. 5. The token ownership service is one of the services provided by centralized services 610 (e.g., which can include a search service and a router service).

As depicted in FIG. 6, ownership tokens are stored in ownership records within an ownership table 630 in a database of the token ownership service 620. The ownership tokens within the database are exposed to the rest of the health information exchange via set of web services 650. The ownership token is a combination of a unique electronic health record identifier (identifying an electronic health record) and a unique location identifier (identifying a location that currently owns the electronic health record). In a specific implementation, the unique electronic health record identifier and the unique location identifier are GUIDs (globally unique identifiers).

In order to control access to electronic health records, the token ownership service 620 imposes access controls (e.g., as defined by business rules 640). In a specific implementation, the token ownership service 620 uses pessimistic locking (exclusive locking) to control access to electronic health records. In the specific implementation, a pessimistic lock must be obtained from the token ownership service 620 before a location can modify (e.g., edit or update) an electronic health record. Using pessimistic locking of ownership records guarantees that only one location (the current owner, as identified by the unique location identifier of the ownership record) is authorized to modify the electronic health record (the specific electronic health record identified by the unique health record identifier of the ownership record). This pessimistic behavior (exclusive locking) provides high integrity and clarity of the location and ownership of EHRs. Other locations have read-only access to the electronic health record, even while it is currently owned by another location.

In a specific implementation, the token ownership lifecycle begins with creation of an EHR at any participating location. As soon as the EHR is created, a message is sent from the originator location to the token ownership service 620 with the newly created EHR GUID and location GUID. The token ownership service 620 then creates a new ownership record entry in the ownership table 630 with a newly created EHR GUID and location GUID (the newly created ownership token). At this point the ownership token becomes available for requests to either view (read-only) the EHR or transfer ownership of the EHR. Transfer of ownership of the EHR can occur by updating the location identifier field of the ownership record with the unique location identifier of the new owner (e.g., as part of a three-way transaction that includes pessimistic locking). Transfer of ownership of the EHR can also occur by creating a new ownership token (for the unique EHR identifier and new unique location identifier) and inserting a corresponding ownership record in the ownership table 630 and deleting the existing ownership record (e.g., in one database transaction to ensure consistency) (e.g., as part of a three-way transaction that includes pessimistic locking).

In a specific implementation, the ownership table 630 is hosted by a reliable and durable service (for example, Microsoft® SQL Server® or Oracle® Database) and exposed via highly available web services 650 (for example Microsoft® .Net™).

VI. Example Enterprise Messaging Server

Figure 7:
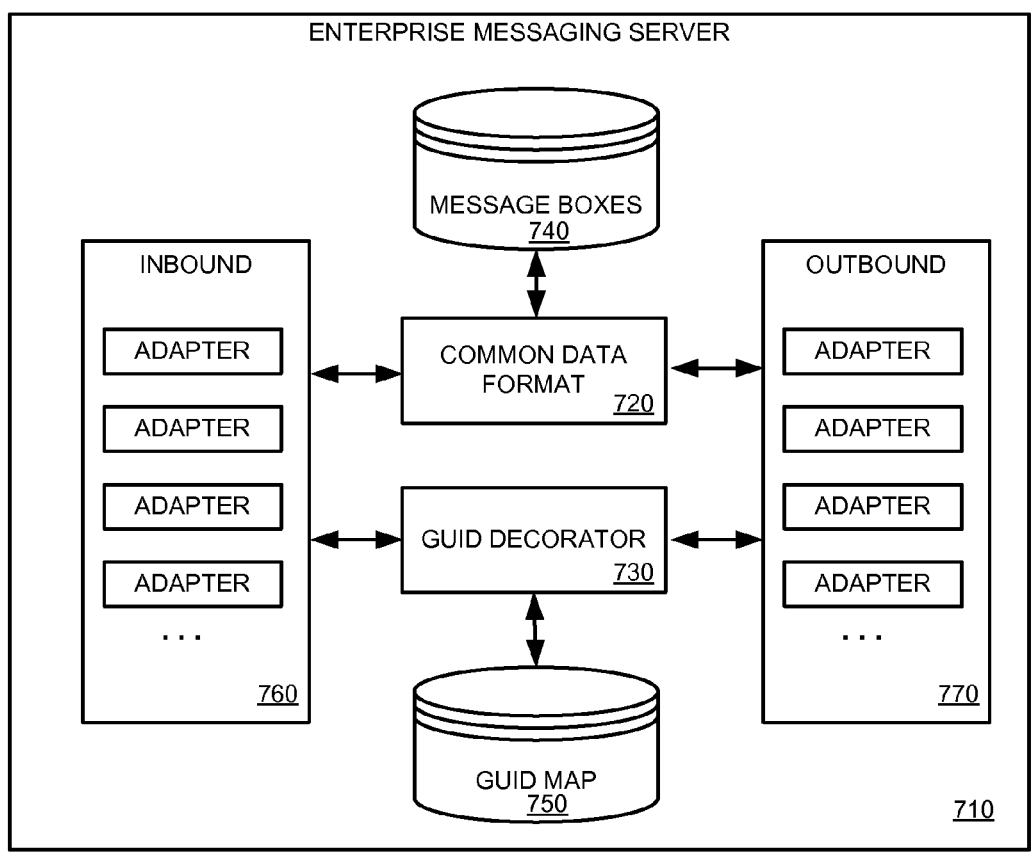
FIG. 7 is a diagram showing an example enterprise messaging server.

FIG. 7 shows an example enterprise messaging server 710. For example, the enterprise messaging server 710 can be the enterprise messaging server depicted at 570 in FIG. 5.

Also depicted in FIG. 7 is a data flow diagram for a data mapping strategy to enable EHR systems with different interfaces and data contracts to view and exchange EHR ownership. The mapping strategy is based on a set of inbound adapters 760 and outbound adapters 770, designed to map data from every format to a common data format 720 and back. EHR solutions may use different data structures to describe patient information (table names, field names, data types) and communicate only through adapters designed for that specific solution. The common data format 720 contains data needed to participate in the EHR sharing solutions described herein plus non-structured data storage for optional data elements. Having additional non-structured data storage (for example XML) minimizes data loss. Pluggable adapter architecture (pairs of matching inbound adapters 760 and outbound adapters 770) provides an extensible and scalable solution for adding new EHR providers into an already existing enterprise of participating locations. Pass-through messages are persisted into the message box database 740 (for example, Microsoft® SQL Server® or Oracle® Database) to provide transactional behavior and durability.

In a specific implementation, the EHR solutions participating in health information exchange are required to pass globally unique identifiers (GUIDs) representing each data element within message data set. Some EHR solutions do not use GUIDs, and instead utilize other types of identifiers (for example integer or alphanumeric identifiers). Messages sent from solutions with non-GUID data type identifiers must be decorated with GUIDs (using the GUID decorator 730 and GUID map 750) before these messages can enter the enterprise messaging server 710. This decoration process takes place at the inbound adapter 760 and outbound adapter 770 stage using the GUID decorator 730 to ensure that all messages adhere to the common data format 720 and contain a GUID. The purpose of having a GUID for all data identifiers is to eliminate the risk of any collision or constraint violation during CRUD database operations, specifically if foreign records are inserted. Some EHR solutions already utilize GUID and can pass that identity to the adapter, eliminating any need for decoration.

VII. Example Health Information Exchange

Figure 8:
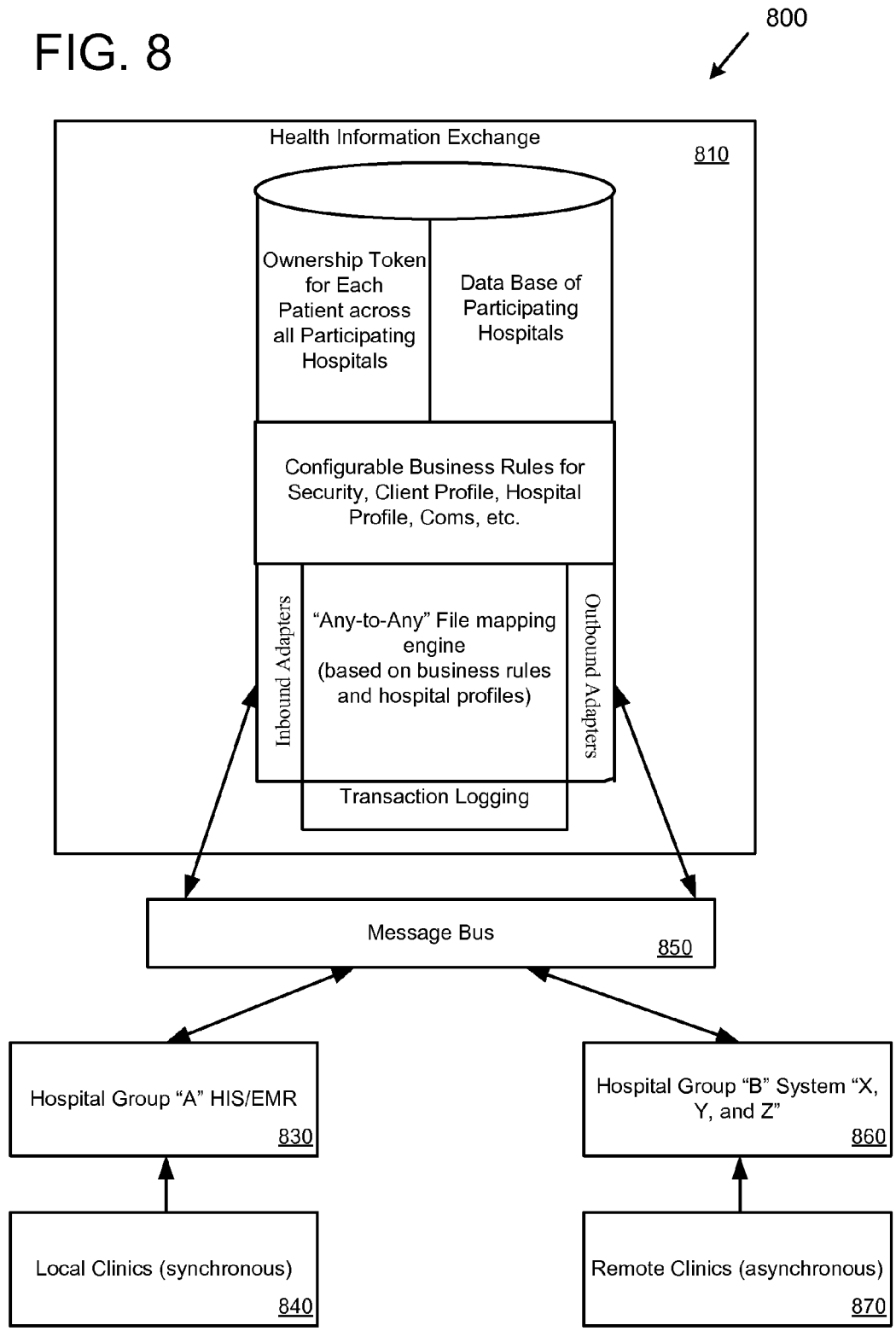
FIG. 8 is a diagram showing an example health information exchange.

FIG. 8 shows an example health information exchange system 800 for providing electronic health record sharing solutions to different types of locations. In the health information exchange system 800, there are two hospital groups depicted: hospital group "A" 830 and hospital group "B" 860. Hospital groups A 830 and B 860 want to exchange information on the clients they share in common. Both groups use different health information systems (HIS) and electronic health record systems. In particular, hospital group B 860 uses three different EHR systems, X, Y and Z. Hospital group A 830 has several local clinics 840 synchronously connected to its main hospital location and EHR system via high speed communication lines. Hospital group B 860 has remote clinics 870 connected asynchronously, meaning they do not have real time access to the centralized HIS/EHR systems but do update EHR data through some manual process well after the point of care transactions have occurred. Both hospital groups (830 and 860) can exchange data (e.g., using HL7 (Health Level Seven International) and DICOM (Digital Imaging and Communications in Medicine), and possibly also fax and paper files), but find that the resulting EHR information is often incomplete, unreliable, and it is uncertain that the most current data is actually in the record. To solve this issue they have joined the health information exchange system 800.

In a specific implementation, the health information exchange (HIE) 810 imposes a requirement (e.g., a business rule) that a patient can only be checked in to one location (e.g., one facility) at a time. Once checked in at that location, no other location can update the electronic health record of the patient (although other locations can read the electronic health record). A location can be a hospital system, a department within a hospital (e.g. a radiology department within a hospital), or another healthcare related location depending on the structural arrangement and needs of the HIE 810. For example, when a patient checks in to hospital A 830, then hospital A 830 needs to obtain ownership of the patient's EHR from the token ownership service before hospital A 830 can update the record. If the patient's EHR was previously owned by hospital B 860, then hospital A 830 would send a request to hospital B 860 and receive the EHR. Once the EHR is received, then hospital A 830 would complete the transfer of ownership (e.g., involving a three-way transaction between hospital A 830, hospital B 860, and the HIE 810). Once the ownership token is obtained by hospital A 830, hospital B's 860 system must mark it as locked (e.g., read-only) meaning hospital B 860 can only read/view the record and not make changes. Note also that hospital B 860 cannot obtain the ownership token until the patient has checked out of Hospital A 830.

In other implementations, there is no requirement imposed by the HIE 810 that other locations cannot obtain ownership of the EHR while a patient is checked in to another location. For example, a patient could be checked in to hospital A 830, while hospital B 860 needs to update the patient's EHR (e.g., due to results of a lab test). Hospital B 860 could obtain ownership of the EHR from the HIE 810, and so long as hospital A 830 is not currently modifying the EHR, the ownership could be transferred to hospital B 860. Hospital A 830 would then need to re-acquire ownership if updates to the record need to be made by hospital A 830.

The health information exchange 810, by supporting electronic health record sharing between providers, can avoid duplicate or redundant work (e.g. duplicate laboratory tests and imaging studies) and reduce the total cost of care. In addition, having one up-to-date electronic medical record across all providers (e.g., a longitudinal medical record) improves the overall standard of care.

The health information exchange 810, via inbound and outbound adapters, can support various information (e.g., health record related) standards. Using the adapters, the HIE 800 can map data from "any to any" EHR system using the HIE 800 chosen standards as the middle tier information exchange broker. The HIE 800 is also responsible for maintaining the messaging environment as well as the centralized data base of business rules, participating hospitals, and centralized services (e.g., search service and token ownership service).

Using the example health information exchange system 800, an issue arises when a patient from hospital group B 860 checks in to hospital group A 830. Using the health record sharing technologies described herein, hospital group A 830 searches for the patient electronic health record in the centralized ownership token database maintained by the HIE 810. The patient search may be done at a logical level by many elements (e.g., name, phone number, address, SSN, provider customer number, etc.) and can be validated by the presentation of a government issued picture ID or other form of identification. The HIE 810 may issue its own form of identification (e.g., an identification card) and the participating hospitals may have their own ID's as well. At the physical level, globally unique identifiers have been generated by the originator EHR vendor's system to uniquely identify records belonging to this patient across all systems of the HIE 810.

In a specific implementation, from a processing perspective, the ETL (Extract, Transform and Load) operations germane to record sharing run in real time and only on request for a specific patient's medical records and only at the time of need. This is an important concept in that the ETL is not a nightly batch update to a central data warehouse of all EHR patient's data, as is most often the case in other health systems. This is a real time provision of only the data requested. This minimizes bandwidth and response time, and limits the data shared to only those clients that the two hospital groups have in common. Data is transferred over an enterprise message bus 850 provided by any current commercial product (such as Microsoft® BizTalk® or IBM® WebSphere®). This messaging infrastructure is redundant, reliable durable and secure.

In a specific implementation, when a patient is checked in to hospital A 830, for example, the centralized token ownership database is updated to reflect that hospital A 830 now "owns" the patient's EHR. Note that this is only a "logical" ownership of the patient data. The patient's preferred hospital and preferred physician could remain in hospital B 860, for example. When the patient returns to hospital B 860 (after a series of tests performed at hospital A 830, for example), the token ownership can be obtained by hospital B 860 at check in, and hospital B 860 can see all of the updates to the EHR performed by hospital A 830. Hospital A's 830 system would mark the patient files as view only when it relinquishes ownership of the token. In a specific implementation, medical notes from either hospital can never be changed, only appended to.

VIII. Example Computing Device

The techniques and solutions described herein can be performed by software and/or hardware of a computing environment, such as a computing device. For example, computing devices include server computers, desktop computers, laptop computers, notebook computers, netbooks, tablet devices, mobile devices, and other types of computing devices.

Figure 9:
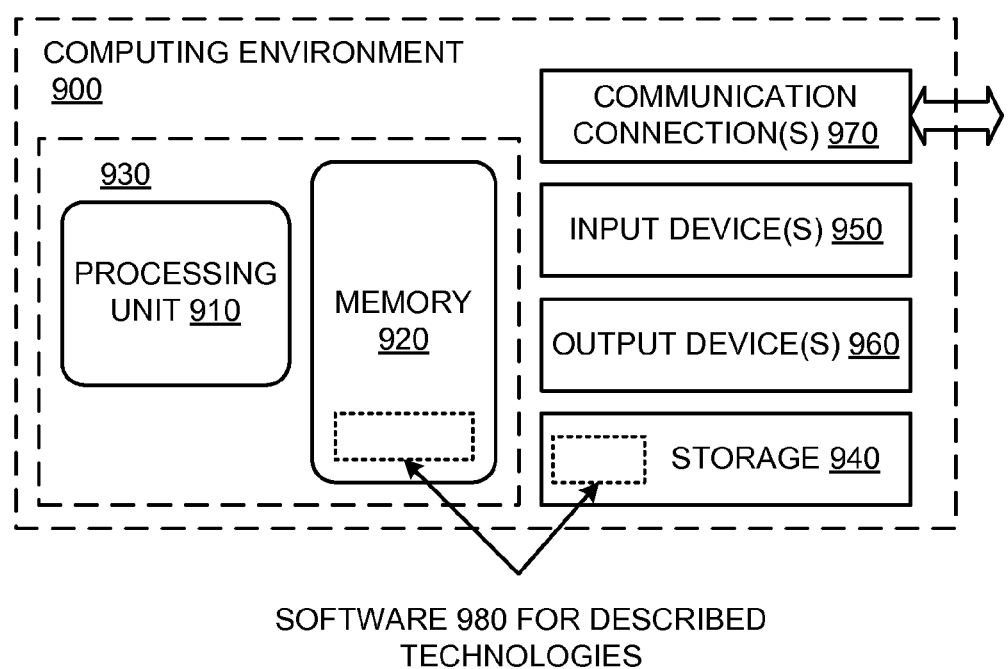
FIG. 9 is a block diagram showing an example computing environment.

FIG. 9 illustrates a generalized example of a suitable computing environment 900 in which described embodiments, techniques, and technologies may be implemented. The computing environment 900 is not intended to suggest any limitation as to scope of use or functionality of the technology, as the technology may be implemented in diverse general-purpose or special-purpose computing environments. For example, the disclosed technology may be implemented using a computing device (e.g., a server, desktop, laptop, hand-held device, mobile device, PDA, etc.) comprising a processing unit, memory, and storage storing computer-executable instructions implementing the electronic health record sharing technologies described herein. The disclosed technology may also be implemented with other computer system configurations, including hand held devices, multi-processor systems, microprocessor-based or programmable consumer electronics, network PCs, minicomputers, mainframe computers, a collection of client/server systems, and the like. The disclosed technology may also be practiced in distributed computing environments where tasks are performed by remote processing devices that are linked through a communications network. In a distributed computing environment, program modules may be located in both local and remote memory storage devices.

With reference to FIG. 9, the computing environment 900 includes at least one central processing unit 910 and memory 920. In FIG. 9, this most basic configuration 930 is included within a dashed line. The central processing unit 910 executes computer-executable instructions and may be a real or a virtual processor. In a multi-processing system, multiple processing units execute computer-executable instructions to increase processing power and as such, multiple processors can be running simultaneously. The memory 920 may be volatile memory (e.g., registers, cache, RAM), non-volatile memory (e.g., ROM, EEPROM, flash memory, etc.), or some combination of the two. The memory 920 stores software 980 that can, for example, implement the technologies described herein. A computing environment may have additional features. For example, the computing environment 900 includes storage 940, one or more input devices 950, one or more output devices 960, and one or more communication connections 970. An interconnection mechanism (not shown) such as a bus, a controller, or a network, interconnects the components of the computing environment 900. Typically, operating system software (not shown) provides an operating environment for other software executing in the computing environment 900, and coordinates activities of the components of the computing environment 900.

The storage 940 may be removable or non-removable, and includes magnetic disks, magnetic tapes or cassettes, CD-ROMs, CD-RWs, DVDs, or any other tangible storage medium which can be used to store information and which can be accessed within the computing environment 900. The storage 940 stores instructions for the software 980, which can implement technologies described herein.

The input device(s) 950 may be a touch input device, such as a keyboard, keypad, mouse, pen, or trackball, a voice input device, a scanning device, or another device, that provides input to the computing environment 900. For audio, the input device(s) 950 may be a sound card or similar device that accepts audio input in analog or digital form, or a CD-ROM reader that provides audio samples to the computing environment 900. The output device(s) 960 may be a display, printer, speaker, CD-writer, or another device that provides output from the computing environment 900.

The communication connection(s) 970 enable communication over a communication medium (e.g., a connecting network) to another computing entity. The communication medium conveys information such as computer-executable instructions, compressed graphics information, or other data in a modulated data signal.

IX. Example Alternatives and Variations

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

Any of the disclosed methods can be implemented as computer-executable instructions stored on one or more computer-readable media (tangible computer-readable storage media, such as one or more optical media discs, volatile memory components (such as DRAM or SRAM), or nonvolatile memory components (such as hard drives)) and executed on a computing device (e.g., any commercially available computer, including smart phones or other mobile devices that include computing hardware). By way of example, computer-readable media include memory 920 and/or storage 940. As should be readily understood, the term computer-readable media does not include communication connections (e.g., 970) such as modulated data signals.

Any of the computer-executable instructions for implementing the disclosed techniques as well as any data created and used during implementation of the disclosed embodiments can be stored on one or more computer-readable media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, Adobe Flash, or any other suitable programming language. Likewise, the disclosed technology is not limited to any particular computer or type of hardware. Certain details of suitable computers and hardware are well known and need not be set forth in detail in this disclosure.

Furthermore, any of the software-based embodiments (comprising, for example, computer-executable instructions for causing a computing device to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

The disclosed methods, apparatus, and systems should not be construed as limiting in any way. Instead, the present disclosure is directed toward all novel and nonobvious features and aspects of the various disclosed embodiments, alone and in various combinations and subcombinations with one another. The disclosed methods, apparatus, and systems are not limited to any specific aspect or feature or combination thereof, nor do the disclosed embodiments require that any one or more specific advantages be present or problems be solved. We therefore claim as our invention all that comes within the scope and spirit of these claims.

We claim:

1. A method, implemented at least in part by a computing device, for controlling access to electronic health records using a hybrid architecture, the method comprising:
   obtaining, by a first location from a token ownership service of a centralized service, an ownership token comprising:
      a unique electronic health record (EHR) identifier identifying an EHR of a patient; and
      a unique location identifier identifying a second location, wherein the second location currently owns the EHR, wherein the second location currently stores the EHR, and wherein the first location and the second location are different physical locations;
   sending, from the first location directly to the second location, a request to transfer the EHR stored at the second location;
   receiving, at the first location directly from the second location, the EHR; and
   obtaining, by the first location from the token ownership service and from the second location, ownership of the EHR, wherein the ownership is obtained, at least in part, using a pessimistic lock, and wherein obtaining ownership is required before the first location is authorized to make changes to the EHR;
   wherein the centralized service is part of a centralized architecture, and wherein the first location and the second location are part of a distributed architecture separate from the centralized architecture; and
   wherein the EHR is stored at one or more locations within the distributed architecture, wherein the EHR is owned at no more than one location within the distributed architecture at any given time, and wherein the EHR is not stored at the centralized architecture.

2. The method of claim 1 wherein the obtaining the unique EHR identifier and the unique location identifier comprises:
   sending, from the first location to a search service of the centralized service, a search request, wherein the search request comprises patient identifying information;
   receiving, by the first location from the search service based on a lookup performed by the search service using the patient identifying information, the unique EHR identifier and the unique location identifier.

3. The method of claim 1 wherein the obtaining ownership of the EHR comprises performing a three-way transaction among the first location, the second location, and the token ownership service to commit ownership change from the second location to the first location.

4. The method of claim 3 wherein performing the three-way transaction comprises:
   if the EHR is locked for editing at the second location, denying ownership change from the second location to the first location; and
   if the EHR is not locked for editing at the second location, allowing ownership change from the second location to the first location.

5. The method of claim 1 wherein the receiving the EHR comprises:
   receiving, by the first location from the second location, a compressed EHR package comprising patient information, medical information, and financial information for the patient.

6. The method of claim 1 wherein the request to transfer the EHR is sent from the first location to the second location via a peer-to-peer network connection between the first location and the second location, and wherein the EHR is received at the first location from the second location via the peer-to-peer network connection.

7. The method of claim 1 wherein the centralized architecture stores patient identifying information related to the patient, wherein the patient identifying information is a subset of patient information stored in the EHR.

8. The method of claim 1 further comprising, after obtaining, by the first location, ownership of the EHR:
   receiving, at the first location from a third location, a request for the EHR; and
   sending, from the first location directly to the third location, a read-only copy of the EHR;
   wherein ownership of the EHR remains at the first location, and wherein the third location is not authorized to make changes to the EHR.

9. A system, comprising one or more computing devices, for controlling access to electronic health records using a hybrid architecture, the system comprising:
   a token ownership service as part of a centralized service of a centralized architecture, the token ownership service configured for:
      storing an ownership token, wherein the ownership token comprises:
         a unique electronic health record (EHR) identifier identifying an EHR of a patient; and
         a unique location identifier, associated with the unique EHR identifier, identifying a first location, of a plurality of locations, wherein the first location currently owns the EHR of the patient; and
      transferring ownership of the EHR from the first location to a second location of the plurality of locations, wherein the transferring ownership comprises changing the unique location identifier of the ownership token to the second location, wherein transfer of ownership is required before the second location is authorized to make changes to the EHR, and wherein the first location and the second location are different physical locations; and
   a search service as part of the centralized service of the centralized architecture, the search service configured for:
      storing patient identifying information of the patient, wherein the patient identifying information is associated with the unique EHR identifier of the patient, and wherein the patient identifying information is a subset of patient information stored in the EHR; and
      responding to a search request by looking up the ownership token based on at least some of the patient identifying information;

wherein the centralized architecture provides the centralized service to the plurality of locations, wherein the plurality of locations are part of a distributed architecture, wherein the distributed architecture is separate from the centralized architecture, and wherein the EHR is not stored at the centralized architecture; and wherein the EHR is stored at one or more of the plurality of locations within the distributed architecture, and wherein the EHR is owned at no more than one location within the distributed architecture at any given time.

10. The system of claim 9 wherein the search service is further configured for:

receiving the search request from the second location of the plurality of locations, wherein the search request comprises the at least some patient identifying information;

looking up the ownership token based on the received patient identifying information; and sending the unique EHR identifier and the unique location identifier, based on the ownership token lookup, to the second location.

11. The system of claim 9 wherein the token ownership service is further configured for:

receiving a request from the second location of the plurality of locations to transfer ownership of the EHR to the second location;

transferring ownership of the EHR from the first location to the second location using a three-way transaction involving the first location, the second location, and the token ownership service.

12. The system of claim 9 wherein the token ownership service is further configured for:

transferring ownership of the EHR from the first location to the second location the plurality of locations using, at least in part, a pessimistic lock of the ownership token.

\* \* \* \* \*